United States Patent [19]

Bredeweg et al.

[11] 4,282,183

[45] Aug. 4, 1981

[54] COMBUSTION SYSTEM

[75] Inventors: Roger L. Bredeweg, Stevensville; Larry S. O'Brien, St. Joseph; Charles B. Vallance, Berrien Springs, all of Mich.

[73] Assignee: Leco Corporation, St. Joseph, Mich.

[21] Appl. No.: 958,967

[22] Filed: Nov. 9, 1978

[51] Int. Cl.³ ............................................. G01N 31/12
[52] U.S. Cl. ........................................ 422/78; 422/102
[58] Field of Search ............... 23/230 PC; 422/78, 79, 422/80, 99, 102

[56] References Cited

U.S. PATENT DOCUMENTS

| | | | |
|---|---|---|---|
| 1,303,980 | 5/1919 | Sperr, Jr. | 422/78 |
| 2,753,246 | 7/1956 | Shields et al. | 23/230 PC |
| 3,374,064 | 3/1968 | Kolsto | 422/78 |
| 3,694,157 | 9/1972 | Koch et al. | 23/230 PC |
| 3,734,693 | 5/1973 | Petcoff | 23/230 PC X |
| 3,957,441 | 5/1976 | Baba | 23/230 PC X |

*Primary Examiner*—Arnold Turk

*Attorney, Agent, or Firm*—Price, Heneveld, Huizenga & Cooper

[57] ABSTRACT

A combustion system includes a cylindrical horizontally extending ceramic combustion tube positioned in a furnace. The combustion tube is enclosed at one end and open at the opposite end for receiving a combustion boat carrying a sample to be combusted for subsequent analysis. The tube also receives a support block loosely positioned along the bottom of the tube and contacting the enclosed end for centering the combustion boat and for supporting one end of a sample withdrawal tube with an open end extending in the space surrounding the combustion boat and having an opposite end extending from the combustion tube. A lance tube also extends into the combustion tube for directing the flow of an oxidizing gas such as oxygen into the combustion boat to facilitate oxidation of a sample. The open end of the combustion tube is effectively sealed by a curtain of gas supplied by a flood tube having a plurality of longitudinally and angularly spaced slots and supplied with a suitable gas for blocking the open end of the tube from admission of atmospheric contaminants and preventing the escape of gasses from the combusted sample.

35 Claims, 4 Drawing Figures

4,282,183

COMBUSTION SYSTEM

BACKGROUND OF THE INVENTION

The present invention relates to combustion systems and particularly to an improved combustion tube for use in combusting a solid or liquid specimen to a gaseous sample for subsequent analysis.

In existing analyzers such as Model No. IR-33 sulphur determinator, commercially available from Leco Corporation of St. Joseph, Mich., the sulphur content of coal, coke, or other substances can be determined from a solid or liquid specimen which is positioned in an induction furnace and combusted to provide a gaseous sample. The gaseous sample is subsequently analyzed by an infrared detector detecting the sulphur dioxide concentration which is then displayed by a digital display as the sulphur content of the specimen. Certain aspects of the combustion system used in such prior art is disclosed in U.S. Pat. No. 3,923,464, issued Dec. 2, 1975, to Sitek, et al, and assigned to the present assignee.

Such systems are open ended and employ a carrier gas introduced into the combustion chamber of the induction furnace to oxidize the specimen and carry the resultant specimen gasses through the opposite end of the combustion chamber and through an infrared cell for detection. A closed loop combustion system of this general type is described in U.S. Pat. No. 3,985,505, issued Oct. 12, 1976, to R. L. Bredeweg, and assigned to the present assignee.

Although these systems provide excellent results in analyzing a specimen, coal cannot be heated directly with radio frequency energy used in these devices since it is a nonconductor. As a result, accelerating agents such as iron chips or powder or tungsten are required to be added to the sample. Further, the combustion chamber in such systems is relatively small and due to the fact that the coal is naturally combustible and creates an exothermic reaction during its combustion, it tends to sputter and some of the specimen can easily escape from the hot zone of the combustion chamber and not be broken down to provide an accurate analysis.

Horizontally extending combustion chambers of the open cylinder type are known in the prior art and represented by Leco Model No. 100 furnace. Although providing a resistance furnace not requiring sample material to be conductive and providing a large hot zone so that the materials cannot escape combustion, such prior art combustion systems were open at both ends and provided a flowthrough system. During operation, the ends had to be plugged to prevent escape of the specimen gas and/or admittance of ambient gasses. Such plugs naturally include the supply and exhaust conduits. This resulted in inconvenient operator access. Also, in the event that this type of system developed a leak in the combustion chamber, the positive pressure within the system could allow some of the specimen gas to escape and therefore not be analyzed. Also, with such systems, the delivery tube from the combustion chamber to the analyzer was spaced from the hot zone of the combustion chamber and recondensation of the specimen gas could occur reducing the amount of specimen being analyzed and thereby providing erroneous results.

SUMMARY OF THE PRESENT INVENTION

The present invention overcomes the difficulties of the prior art noted above by providing a horizontally extending combustion chamber having a relatively large hot zone and an open end for receiving a combustion boat containing the specimen to be analyzed and an enclosed opposite end. The specimen gas is withdrawn from near the closed end of the combustion chamber by an eduction tube extending within the combustion chamber thereby preventing recondensation of the specimen gas. In the preferred embodiment of the combustion system, the open end of the combustion chamber is effectively sealed by a gas curtain such that the interior of the combustion chamber is available to the operator for readily inserting and removing specimens for combustion.

These and other features, advantages and objects of the present invention can best be understood by reference to the following description thereof, together with the drawings, in which:

DETAILED DESCRIPTION OF THE PREFERRED EMBODIMENT

Figure 1:
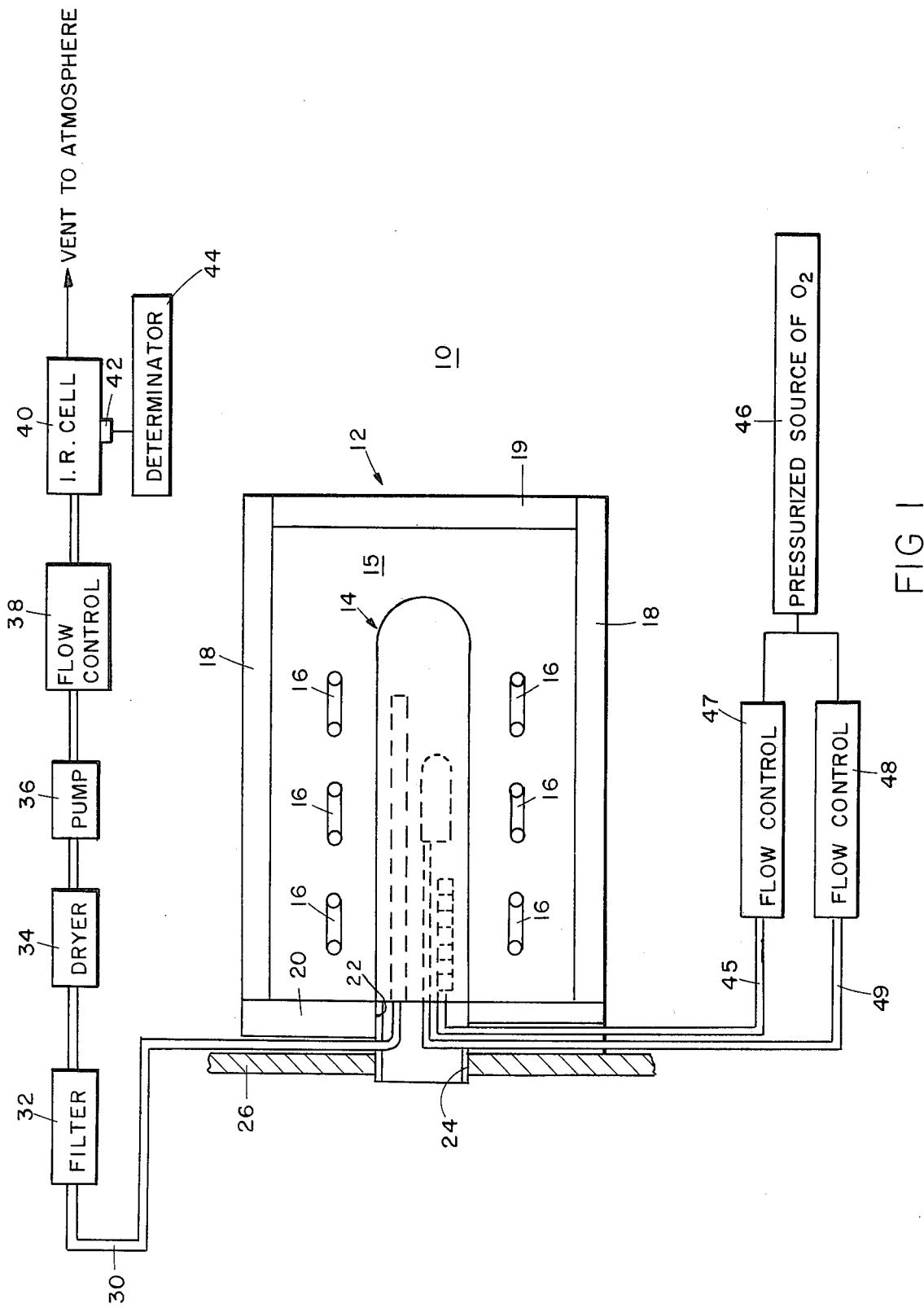
FIG. 1 is an analyzer incorporating the combustion system of the present invention shown partly in schematic and block diagram form.

Referring initially to FIG. 1, there is shown an analyzer 10 which, in the preferred embodiment, is employed for determining the percentage sulphur content in coal and coke. Although the preferred embodiment is used with these solid materials which are pulverized into powder form for combustion, it is to be understood that the combustion apparatus of the present invention can be used with other solid or liquid materials and for determining other constituent elements of a given specimen.

The analyzer 10 comprises a combustion furnace 12 shown in a top plan view partly broken away in FIG. 1 and including a combustion chamber 14 positioned within the furnace. Furnace 12 is a resistance type furnace having six generally U-shaped resistance heating elements 16, three of which are positioned adjacent and on opposite sides of the combustion chamber 14. The heating elements and combustion chamber are housed within a refractory box including sidewalls 18, a rear wall 19, and a front wall 20 having an access opening 22 for the extension of one end of the combustion chamber through an access port 24 in the instrument's front panel 26. The refractory lining of the furnace 12 also includes a floor 15 and a top (not shown in the drawing). Thus, the combustion chamber 14 is totally enclosed within the resistance furnace 12. The resistance heating elements 16 are preferably KANTHAL ® type resistance elements made of molybdenum disilicide and provide heating temperatures to the interior of the combustion chamber 14 in excess of 2000° F. with the maximum temperature being in the neighborhood of 2800° F.

Gas from the specimens being combusted within the combustion chamber are withdrawn by an eduction tube 30 which, as described in greater detail below, extends into the combustion chamber 14 and communicates with a filter 32 including a quartz wool filter media for removing smoke and precipitates from the specimen gas. The output of filter 32 is coupled to an anhydrous dryer 34 for removing water from the specimen gas. The output of dryer 34 is coupled to the input of a pump 36 for drawing the specimen gas through the filter and dryer and from the combustion chamber 14 through the eduction tube 30. The output of the pump 36 is coupled to a flow control 38 for providing a flow rate of approximately three liters per minute to the input of an IR cell 40. The output of IR cell 40 is vented to the atmosphere. IR cell 40 includes a detector 42 which is electrically coupled to a determinator 44 including electrical circuits for processing the electrical signals from detector 42 and providing a digital readout of the percentage of sulphur content in the specimen being combusted. The determinator 44 elements 32 through 44 are of construction generally well known and can be of the type disclosed in the above identified U.S. Pat. No. 3,985,505, the disclosure of which is incorporated herein by reference. Naturally, modifications to the specific electrical circuitry can be made to accommodate the system for the particular specimen gas being analyzed. In the preferred embodiment, the IR cell includes an $SO_2$ filter for the detection of sulphur dioxide which is the combination of the element sulphur and the oxidizing gas oxygen employed in the system of the preferred embodiment.

The analyzer further includes a pressurized source 46 of oxygen gas coupled to a pair of flow controllers 47 and 48 which supply the oxidizing gas to the combustion chamber 14 by supply conduits 45 and 49, respectively. Thus, the specimen material is combusted by the furnace 12 in the presence of oxygen to convert the sulphur contained within the specimen to sulphur dioxide for subsequent analysis. Having briefly described the overall environment of the combustion system of the present invention, a detailed description of the combustion chamber 14 is now presented in conjunction with FIGS. 2 through 4.

Figure 2:
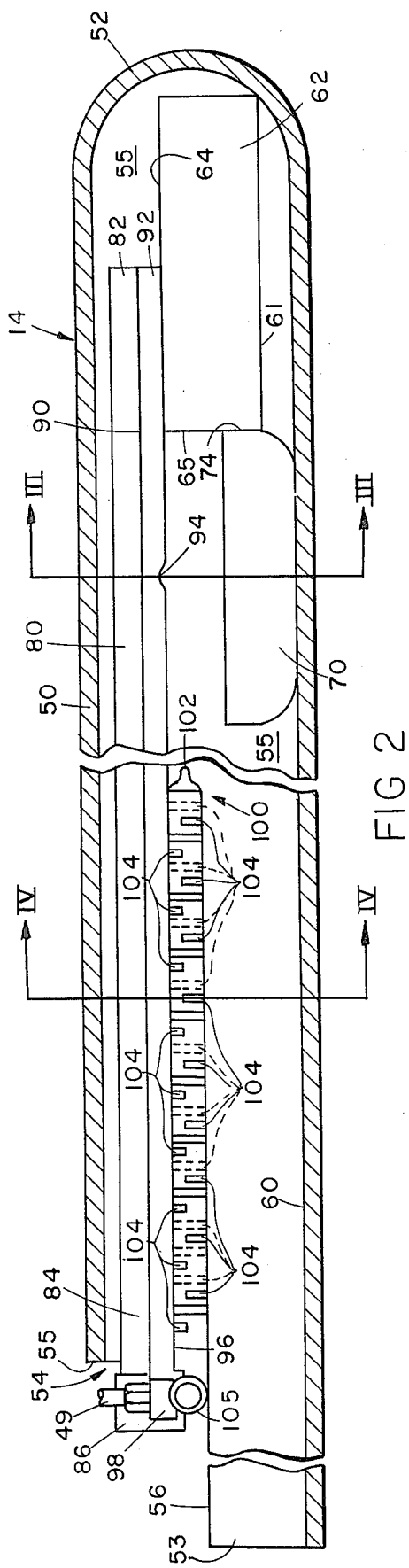
FIG. 2 is a side elevational view partly in cross section of the combustion chamber of the present invention.
Figure 4:
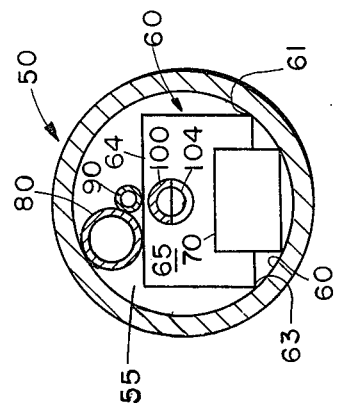
FIG. 4 is a cross-sectional view of the combustion chamber taken along section lines IV—IV of FIG. 2.
Figure 3:
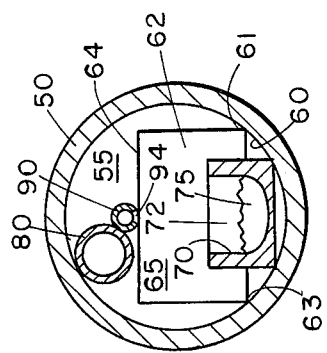
FIG. 3 is a cross-sectional view of the combustion chamber taken along the section lines III—III of FIG. 2.

As seen in FIGS. 2 through 4, the combustion chamber 14 of the present invention comprises a tube 50 of generally cylindrical construction and having a rounded closed first end 52 and an opposite open second end 54. In FIG. 2, tube 50 itself is shown in cross section so as to clearly illustrate the relative position of the various elements of the system. The cylindrical combustion tube 50 is made of relatively thin wall construction and has an inside diameter of approximately 1½ inches with a wall thickness of ⅛ inch. In the preferred embodiment, the combustion tube is made of a ceramic material such as alumina. It could also be made of other suitable refractory material capable of withstanding temperatures of about 2800° F. The tube includes a cutaway segment near the open end to define a pair of generally horizontally extending surfaces 56 (FIG. 2) which extend outwardly from open end 54 a distance of 2.25 inches and provides horizontal support ledges for the sample eduction and oxygen supply tubes. The notch formed by cutting away an upper curved one half segment of the open end of tube 50 also defines semi-annular end walls 53 and 55. The overall length of the combustion tube of the preferred embodiment from wall 53 to end 52 is 18.12 inches. In the construction of the combustion tube, it is desired to keep the length of the tube significantly greater than its diameter so that a relatively long hot zone within the furnace shown in FIG. 1 is provided and the interior of the tube can be effectively sealed using a curtain of gas. Thus, the length to internal diameter ratio of the tube of the preferred embodiment is slightly greater than 12:1.

Combustion tube 50 is adapted to be oriented horizontally within furnace 12 and as such the lower half of the cylindrical interior wall of the tube defines a floor 60 which slidably receives a ceramic block 62. Block 62 is positioned within the tube against the interior curved end 52 as best seen in FIG. 2. The block is of generally rectilinear construction and its lower outer edges 61 and 63 rest on the floor 60 of combustion tube 50 as best seen in FIGS. 3 and 4. Block 62, like tube 50, is slip cast of alumina and provides the dual function of positioning a combustion boat 70 in longitudinally spaced relationship with respect to the first end 52 of the combustion tube 50 and providing a support for the ends of an eduction tube 80 and a lance tube 90 which is best seen in FIG. 3 rest upon the upper surface 64 of block 62.

Block 62 has a height and width as best seen in FIG. 3 to permit the eduction tube 80 to fit between the upper support surface 64 of the block and clear the interior surface of tube 50. End 82 of eduction tube 80 is open and communicates with the interior space 55 of the combustion tube near the end 52 of the tube and between this end and the boat 70 for withdrawing specimen gasses by the negative pressure at the input side of pump 36 (FIG. 1). Thus, opening 82 faces the enclosed end 52 of the combustion tube and draws the specimen gasses from the boat 70 in the direction toward the enclosed end to be educted by the eduction tube 80. End 82 of tube 80 rests freely on surface 64 of the block 62 which permits expansion and contraction of both the combustion tube 50 and eduction tube 80 without cracking which can otherwise occur if they were cemented or otherwise secured together. Thus, by freely resting end 82 of the tube on block 62, the thermal shock during heating of the combustion tube does not cause cracking of the tubes. Similarly, block 62 is slid into the open end of tube 50 and is free to move slightly as the material is heated and/or cooled. The end 84 of tube 80 remote from the open end 82 extends outwardly through the open end 54 of the combustion tube 50 and is coupled to conduit 30 by means of a suitable coupling 86. A conventional support clip (not shown) is employed to support the end 84 of the tube at the top of tube 50 at edges 55 such that tube 80 extends horizontally within tube 50 and parallel to the axis of tube 50. The clip extends upwardly so as not to interfere with the lower half of opening 54. In the preferred embodiment, eduction tube 80 is a longitudinally extending cylindrical tube having an outside diameter of approximately 7/16 inch and a wall thickness of 3/32 inch and is also slip cast of alumina.

The combustion boat 70 is of generally conventional construction and, as is best seen in FIG. 3, defines an interior space 72 for receiving a specimen 75 for analysis. The combustion boat 70 is made of zirconia and has a height sufficient to present a forward edge 74 which contacts the trailing edge 65 of block 62 which defines a positive stop for the boat 70 thereby positioning it within the combustion tube 50 when the boat is slid into the combustion tube by a suitable push rod (not shown). The height of the boat 70 also permits the boat to fit under the remaining tube structure positioned within the combustion tube and including the eduction tube 80.

In order to promote complete and rapid combustion of the specimen 75, an oxygen lance tube 90 is employed and has an end 92 which is sealed with a suitable ceramic cement such as Sauereisen No. 29 which is commercially available. The enlongated ceramic lance tube 90 is also slip cast of alumina and includes an opening 94 longitudinally positioned to be centered in alignment above the combustion boat 70 as best seen in FIGS. 2 and 3. Like tube 80, end 92 of tube 90 freely rests on the upper surface 64 of ceramic block 62 to permit relative movement between the members during heating and cooling thus preventing cracking of the ceramic bodies. The end 96 of tube 90 remote from end 92 extends through opening 54 and is coupled to the supply line 49 by a connector 98. A conventional stainless steel clip (not shown) supports end 96 to the edge 55 of tube 50 such that it extends horizontally within tube 50 parallel to its axis. Opening 94 in tube 90 faces downwardly and is 0.1 inch in diameter for providing a gentle flow of oxygen into the open boat 70. Flow controller 48 (FIG. 1) is adjusted to provide a flow rate of approximately 1 liter per minute while flow controller 38 provides an eduction rate of 3 liters per minute.

In order to isolate the interior space 55 of the combustion tube from the atmosphere and thus contain the specimen gas completely within the tube, a flood tube 100 is provided and comprises a stainless steel cylindrical tube having one end 102 pinched off and thereby sealed and a plurality of alternately staggered inwardly radially projecting slots 104 cut into the walls of tube 100 approximately midway therethrough and alternately staggered at a 90° angular rotating pattern along the tube. The opposite end 105 of tube 100 extends outwardly through opening 54 in the combustion tube and is coupled to the oxygen supply conduit 45 by means of a suitable coupling (not shown). Flow controller 47 supplies oxygen to the flood tube 100 at a flow rate of approximately 4 liters per minute while the angularly and longitudinally spaced slots 104 swirl the oxygen in a circular path and at a relatively low velocity to provide a curtain of oxygen flow from near the open end 54 of combustion tube 50 inwardly for about 4.2 inches. This effectively seals the combustion tube during its operation. It is noted that when pump 36 is evacuating the specimen through opening 82 in eduction tube 80, the pressure within the combustion tube space 55 is slightly below atmospheric pressure thus drawing a small amount of the air curtain oxygen from slots 104 and tube 100 also over combustion boat 70 to further enhance the oxidation of the specimen. Tube 100, in the preferred embodiment, comprises a stainless steel tube having an inner diameter of 3/16 inch with slots 104 having a width of 0.06 inch corresponding to the curve of the saw used to cut the slots and the space of 0.06 inch between each of the slots. By providing cuts 104 angularly displaced at 90° intervals, a circular dispersion pattern for the flooding oxygen is provided which repeats itself for each successive four slots. The size of the slots prevent excessive gas velocity to prevent undesired turbulence within the tube. Thus, the air curtain flood tube is designed to provide a laminar swirling or circular flow at about the open ¼ length of the open end of tube 50.

With the structure of the preferred embodiment of the invention, therefore, coal or other specimen to be analyzed is heated to a temperature of approximately 2500° F. by the resistive heating element 16 in furnace 12 (FIG. 1) while at the same time oxygen is supplied to the lance tube 90 and to the flood tube 100 both sealing the combustion tube opening 54 and providing a stream of oxygen directly into the combustion boat 70. The specimen gas resulting from the exothermic combustion of the coal and/or coke is drawn in the open end 82 of eduction tube 80 and subsequently supplied to the analyzer including the infrared cell for analysis to provide a readout of the percent by weight of sulphur content contained within the coal.

Naturally, the combustion system of the present invention can be used with other substances to be analyzed and in some cases an atmosphere other than oxygen would be used for reacting with the specimen to provide combustion of the specimen into its constituent gaseous elements. It may be possible in some applications of the device to operate the combustion system itself without the flooding tube 100 and/or the lance 92. Further, the ceramic material employed for manufacturing the combustion tube, the eduction tube, and the lance tube may be of material other than alumina.

These and various other modifications to the preferred embodiment will, however, fall within the spirit and scope of the present invention as defined by the appended claims.

The embodiments of the invention in which an exclusive property or privilege is claimed are defined as follows:

1. A combustion chamber for use in combusting a liquid or solid specimen into a gaseous state for subsequent analysis to determine the amount of one or more constituent elements contained in the specimen comprising:

an elongated combustion chamber having a length significantly greater than its width and adapted to be oriented with its longitudinal axis extending generally horizontally, said chamber being of relatively thin walled construction and continuously open at one end to receive samples to be combusted which are positioned in said chamber through said open end, said chamber including an elongated horizontally extending floor for supporting a sample thereon and enclosed at its opposite end; wherein said combustion chamber is made of a material to withstand temperatures of combustion in excess of 2000° F.; an eduction tube means communicating with the interior of said chamber for withdrawing specimen gases therefrom from a position closer to said enclosed end than to said open end; and means for providing a sealing curtain of gas near said continuously open end of said combustion chamber.

2. The combustion chamber as defined in claim 1 and further including stop means positioned in said combustion chamber to locate a specimen holding combustion boat in spaced relationship from said enclosed end.

3. The combustion chamber as defined in claim 2 and further including lance means positioned in said combustion chamber for directing a reactive gas into a combustion boat to facilitate combustion of the specimen.

4. The combustion chamber as defined in claim 1 wherein said combustion chamber comprises a cylindrical member.

5. The combustion chamber as defined in claim 4 wherein said combustion chamber is made of a ceramic material.

6. The combustion chamber as defined in claim 5 wherein the length of said cylindrical member is about 19 inches and the internal diameter of said member is about 1.5 inches.

7. The combustion chamber as defined in claim 6 wherein said combustion chamber is cut away at said open end to provide a pair of spaced horizontally extending ledges extending from said open end.

8. The combustion chamber as defined in claim 7 wherein said ceramic material comprises alumina.

9. A combustion chamber for use in combusting a liquid or solid specimen into a gaseous state for subsequent analysis to determine the amount of one or more constituent elements contained in the specimen comprising:

an elongated combustion chamber having a length significantly greater than its width and adapted to be oriented with its longitudinal axis extending generally horizontally, said chamber being of relatively thin walled construction and continuously open at one end to receive samples to be combusted which are positioned in said chamber through said open end, said chamber including an elongated horizontally extending floor for supporting a sample thereon and integrally formed to be closed at its opposite end; and wherein said combustion chamber is made of a material to withstand temperatures of combustion in excess of 2000° F.;

an eduction tube means communicating with the interior of said chamber for withdrawing specimen gasses therefrom from a position closer to said enclosed end than to said open end;

stop means positioned in said combustion chamber to locate a specimen holding combustion boat in spaced relationship from said enclosed end;

lance means positioned in said combustion chamber for directing a reactive gas into a combustion boat to facilitate combustion of the specimen; and means for providing a sealing curtain of gas at said open end of said combustion chamber.

10. The combustion chamber as defined in claim 9 wherein said means for providing a curtain of gas comprises a tube extending into said open end of said combustion chamber and having a plurality of radially and axially spaced apertures therein for flooding the open end of said tube with a gas supplied to said tube.

11. For use in a gas analysis system whereby a solid or liquid specimen is combusted to provide a gaseous sample for subsequent analysis to determine the amount of one or more constituent elements contained in the sample, a combustion system comprising:

an elongated combustion chamber of integral construction having one end enclosed and the remaining end continuously open for admitting samples therein, said chamber including an interior horizontally extending, elongated floor for supporting a sample, and means communicating with the interior of said chamber near the enclosed end for withdrawing specimen gasses from the interior of said combustion chamber; and means for providing a sealing curtain of gas near said continuously open end of said combustion chamber.

12. The combustion system as defined in claim 11 wherein said means for withdrawing specimen gasses from said combustion chamber comprises an eduction tube having an open end communicating with the interior of said chamber closer to the enclosed end than to the open end thereof and an opposite end for delivering gas from said combustion chamber to an analyzer.

13. For use in a gas analysis system whereby a solid or liquid specimen is combusted to provide a gaseous sample for subsequent analysis to determine the amount of one or more constituent elements contained in the sample, a combustion system comprising:

an elongated combustion chamber of integral construction having one end enclosed and the remaining end continuously open for admitting samples therein, said chamber including an interior horizontally extending, elongated floor for supporting a sample, and means communicating with the interior of said chamber near the enclosed end for withdrawing specimen gasses from the interior of said combustion chamber, wherein said means for withdrawing specimen gasses from said combustion chamber comprises an eduction tube having an open end communicating with the interior of said chamber closer to the enclosed end than to the open end thereof and an opposite end for delivering gas from said combustion chamber to an analyzer; and means for providing a sealing curtain of gas at said open end of said combustion chamber.

14. The combustion system as defined in claim 13 wherein said means for providing a curtain of gas comprises a tube extending into said open end of said combustion chamber and having a plurality of radially and axially spaced apertures therein for flooding the open end of said chamber with a gas supplied to said tube.

15. The combustion system as defined in claim 14 and further including lance means positioned in said combustion chamber for directing a reactive gas into the combustion chamber to facilitate combustion of the specimen.

16. The combustion system as defined in claim 15 and further including stop means positioned in said combustion chamber to locate a specimen holding combustion boat in spaced relationship from said enclosed end.

17. The combustion system as defined in claim 16 wherein said combustion chamber comprises a cylindrical member.

18. The combustion system as defined in claim 17 wherein said combustion chamber is made of a ceramic material.

19. The combustion system as defined in claim 18 wherein the length of said cylindrical member is about 19 inches and the internal diameter of said member is about 1.5 inches.

20. The combustion system as defined in claim 19 wherein said combustion chamber is cut away at said open end to provide a pair of spaced horizontally extending ledges extending from said open end.

21. The combustion system as defined in claim 20 wherein said ceramic material comprises alumina.

22. A combustion chamber for use in combusting a liquid or solid specimen into a gaseous state for subsequent analysis to determine the amount of one or more constituent elements contained in the specimen comprising:

an elongated combustion chamber enclosed at one end and having a length significantly greater than its width and having an interior elongated floor for receiving samples oriented with its longitudinal axis extending generally horizontally, said chamber being of relatively thin walled construction and continuously open at one end to receive samples to be combusted which are slideably positioned in said chamber through said continuously open end on said floor said combustion chamber made of a material to withstand temperatures of combustion in excess of 2000° F., said combustion chamber being provided with a cutaway at said open end to provide a ledge extending from said open end for supporting longitudinally extending eduction and supply tubes and means for providing a sealing curtain of gas at said continuously open end of said combustion chamber.

23. The combustion chamber as defined in claim 22 wherein said means for providing a curtain of gas comprises a tube extending into said open end of said combustion chamber and having a plurality of spaced apertures therein for flooding the open end of said tube with a gas supplied to said tube.

24. The combustion chamber as defined in claim 23 wherein said apparatus are spaced axially and radially along said tube.

25. A combustion system for use in combusting a liquid or solid specimen into a gaseous state for subsequent analysis to determine the amount of one or more constituent elements contained in the specimen comprising:
an elongated combustion chamber having a length significantly greater than its width, said chamber being of relatively thin walled construction and continuously open at one end to receive samples to be combusted which are positioned in said chamber through said open end, said combustion chamber made of a material to withstand temperatures of combustion in excess of 2000° F., furnace means for heating said combustion chamber;
means for mounting said combustion chamber within said furnace means with its longitudinal axis extending generally horizontally; and means for providing a gaseous seal at said continuously open end of said combustion chamber.

26. The combustion chamber as defined in claim 25 wherein the end opposite said continuously open end is enclosed and further including eduction tube means communicating with said combustion chamber for withdrawing specimen gasses therefrom from a position closer to said enclosed end than to said open end.

27. The combustion chamber as defined in claim 26 and further including stop means positioned in said combustion chamber to locate a specimen holding combustion boat in spaced relationship from said enclosed end.

28. The combustion chamber as defined in claim 27 and further including lance means positioned in said combustion chamber for directing a reactive gas into the combustion boat to facilitate combustion of the specimen.

29. The combustion chamber as defined in claim 25 wherein said combustion chamber comprises a cylindrical member having an enclosed end opposite said open end.

30. The combustion chamber as defined in claim 29 wherein said combustion chamber is made of a ceramic material.

31. The combustion chamber as defined in claim 30 wherein the length of said cylindrical member is about 19 inches and the internal diameter of said member is about 1.5 inches.

32. The combustion chamber as defined in claim 31 wherein said combustion chamber is cut away at said open end to provide a pair of spaced horizontally extending ledges extending from said open end.

33. The combustion chamber as defined in claim 32 wherein said ceramic material comprises alumina.

34. A combustion system for use in combusting a liquid or solid specimen into a gaseous state for subsequent analysis to determine the amount of one or more constituent elements contained in the specimen comprising:
an elongated cylindrical combustion chamber made of alumina having a length of about 19 inches and an internal diameter of about 1.5 inches, said chamber being of relatively thin walled construction and continuously open at one end to receive samples to be combusted which are positioned in said chamber through said open end, said combustion chamber having an enclosed end opposite said open end and made of a material to withstand temperatures of combustion in excess of 2000° F.;
furnace means for heating said combustion chamber;
means for mounting said combustion chamber within said furnace means with its longitudinal axis extending generally horizontally wherein said combustion chamber is cut away at said open end to provide a pair of spaced horizontally extending ledges extending from said open end and wherein the end opposite said continuously open end is enclosed and further including eduction tube means communicating with said combustion chamber for withdrawing specimen gasses therefrom from a position closer to said enclosed end than to said open end;
stop means positioned in said combustion chamber to locate a specimen holding combustion boat in spaced relationship from said enclosed end;
lance means positioned in said combustion chamber for directing a reactive gas into the combustion boat to facilitate combustion of the specimen; and
means for providing a sealing curtain of gas at said open end of said combustion chamber.

35. The combustion chamber as defined in claim 34 wherein said means for providing a curtain of gas comprises a tube extending into said open end of said combustion chamber and having a plurality of radially and axially spaced apertures therein for flooding the open end of said tube with a gas supplied to said tube.

* * * * *

UNITED STATES PATENT AND TRADEMARK OFFICE
CERTIFICATE OF CORRECTION

PATENT NO. : 4,282,183
DATED : August 4, 1981
INVENTOR(S) : Roger L. Bredeweg et al It is certified that error appears in the above—identified patent and that said Letters Patent is hereby corrected as shown below:

Column 4, line 45:

"edges" should be --edge--

Column 9, line 12:

"apparatus" should be --apertures--

Signed and Sealed this

Twenth-eighth Day of September 1982

[SEAL]

Attest:

GERALD J. MOSSINGHOFF

Attesting Officer    Commissioner of Patents and Trademarks